(12) United States Patent
Rim et al.

(10) Patent No.: US 10,987,425 B2
(45) Date of Patent: Apr. 27, 2021

(54) LIQUID FORMULATION OF LONG-ACTING HUMAN GROWTH HORMONE IMMUNOGLOBULIN CONJUGATE

(71) Applicant: HANMI PHARM. CO., LTD., Hwaseong-si (KR)

(72) Inventors: Hwa Peoung Rim, Seoul (KR); Hyun Uk Kim, Busan (KR); Ho Taek Im, Yongin-si (KR); Sang Yun Kim, Gimpo-si (KR); Hyung Kyu Lim, Hwaseong-si (KR); Sung Min Bae, Seongnam-si (KR); Se Chang Kwon, Seoul (KR)

(73) Assignee: HANMI PHARM. CO., LTD., Hwaseong-si (KR)

( * ) Notice: Subject to any disclaimer, the term of this patent is extended or adjusted under 35 U.S.C. 154(b) by 153 days.

(21) Appl. No.: 15/025,127

(22) PCT Filed: Sep. 26, 2014

(86) PCT No.: PCT/KR2014/009059
§ 371 (c)(1),
(2) Date: Mar. 25, 2016

(87) PCT Pub. No.: WO2015/046974
PCT Pub. Date: Apr. 2, 2015

(65) Prior Publication Data
US 2016/0213789 A1   Jul. 28, 2016

(30) Foreign Application Priority Data
Sep. 27, 2013   (KR) .................. 10-2013-0115177

(51) Int. Cl.
| | | |
|---|---|---|
| A61K 38/27 | (2006.01) | |
| A61K 47/26 | (2006.01) | |
| A61K 9/19 | (2006.01) | |
| A61K 9/00 | (2006.01) | |
| A61K 47/68 | (2017.01) | |
| A61K 47/12 | (2006.01) | |
| A61K 47/18 | (2017.01) | |

(52) U.S. Cl.
CPC ............ *A61K 47/26* (2013.01); *A61K 9/0019* (2013.01); *A61K 9/19* (2013.01); *A61K 38/27* (2013.01); *A61K 47/12* (2013.01); *A61K 47/183* (2013.01); *A61K 47/68* (2017.08); *A61K 47/6811* (2017.08); *A61K 47/6883* (2017.08)

(58) Field of Classification Search
None
See application file for complete search history.

(56) References Cited

U.S. PATENT DOCUMENTS

| | | | |
|---|---|---|---|
| 7,592,004 B2 * | 9/2009 | Kaisheva ............. | A61K 9/0019 424/130.1 |
| 7,790,679 B2 * | 9/2010 | Li et al. ........................ | 514/7.7 |
| 2006/0135427 A1 | 6/2006 | Hays et al. | |
| 2008/0125356 A1 | 5/2008 | Wadhwa et al. | |
| 2010/0029569 A1 | 2/2010 | Bjørn et al. | |
| 2013/0115231 A1 | 5/2013 | Hong et al. | |

FOREIGN PATENT DOCUMENTS

| | | |
|---|---|---|
| CN | 103068366 A | 4/2013 |
| EP | 2 606 908 A1 | 6/2013 |
| JP | H10-265404 A | 10/1998 |
| JP | 2001-524360 A | 12/2001 |
| JP | 2005-232177 A | 9/2005 |
| KR | 10-2000-0010630 A | 2/2000 |
| KR | 10-0273053 B1 | 12/2000 |
| KR | 10-0567902 B1 | 4/2006 |
| KR | 10-2006-0106486 A | 10/2006 |
| KR | 10-0725315 B1 | 6/2007 |
| KR | 10-2012-007182 A | 1/2012 |
| RU | 2190129 C2 | 9/2002 |
| RU | 2229288 C2 | 5/2004 |
| WO | 2011/073234 A2 | 6/2011 |
| WO | 2012/008779 A2 | 1/2012 |
| WO | 2013/147559 A1 | 10/2013 |

OTHER PUBLICATIONS

International Searching Authority, International Search Report for PCT/KR2014/009059 dated Jan. 19, 2015 [PCT/ISA/210].
International Searching Authority, Written Opinion for PCT/KR2014/009059 dated Jan. 19, 2015 [PCT/ISA/237].
European Patent Office; Communication dated May 2, 2017 in counterpart European application No. 14847086.7.
State Intellectual Property Office of the P.R.C.; Communication dated Apr. 23, 2018 in counterpart application No. 201480064028.X.
Taiwanese Patent Office; Communication dated Apr. 11, 2018 in counterpart application No. 103133464.
European Patent Office; Communication dated Mar. 8, 2018 in counterpart application No. 14847086.7.
Carpenter, J. F., et al., "Rational Design of Stable Lyophilized Protein Formulations: Theory and Practice", Pharmaceutical Biotechno., vol. 13, Jan. 1, 2002, 23 pages, XP009053337.
Japanese Patent Offcie; Communication dated Jul. 2, 2018 in counterpart application No. 2016-518140.

* cited by examiner

*Primary Examiner* — Christine J Saoud
(74) *Attorney, Agent, or Firm* — Sughrue Mion, PLLC

(57) ABSTRACT

The present invention relates to a sustained type human growth hormone conjugate preparation comprising: a sustained type human growth hormone (hGH) conjugate resulting from conjugation between the immunoglobulin Fc region and a human growth hormone (hGH) constituting a bioactive peptide; a buffer solution; a nonionic surfactant; and a sugar alcohol. More specifically, the present invention relates to a sustained type human growth hormone conjugate freeze dried preparation and liquid preparation, to a production method for the freeze dried preparation, to a method of reconstituting the freeze dried preparation, and to a kit comprising the freeze dried preparation and a reconstituting solution.

6 Claims, 3 Drawing Sheets

[Figure 1]
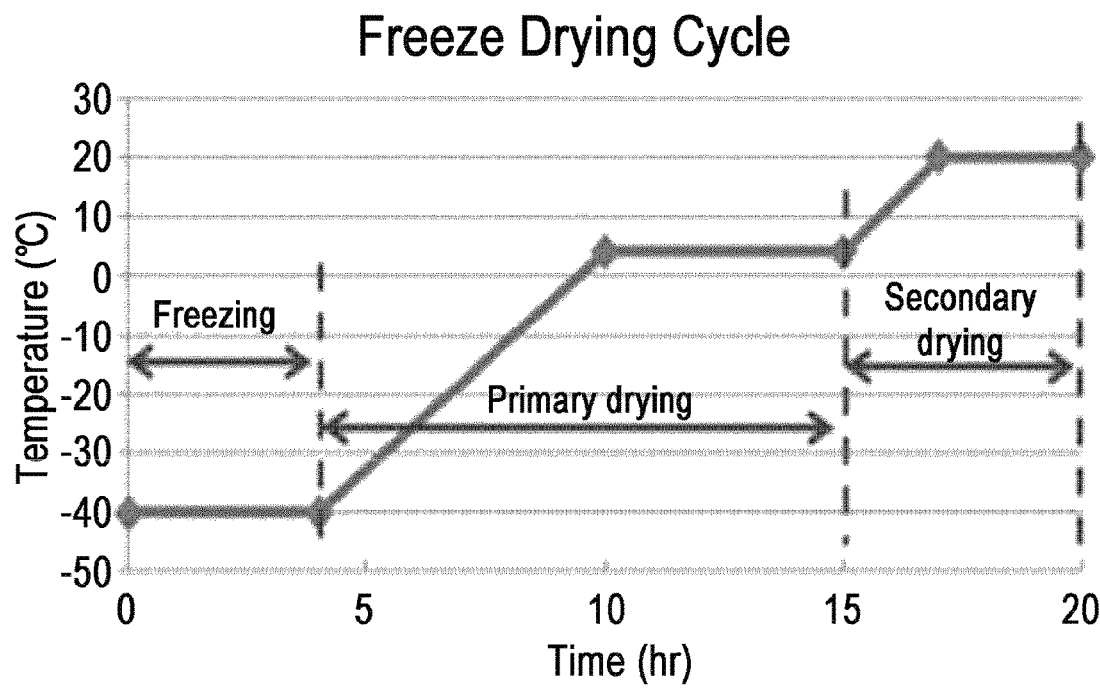

[Figure 2]
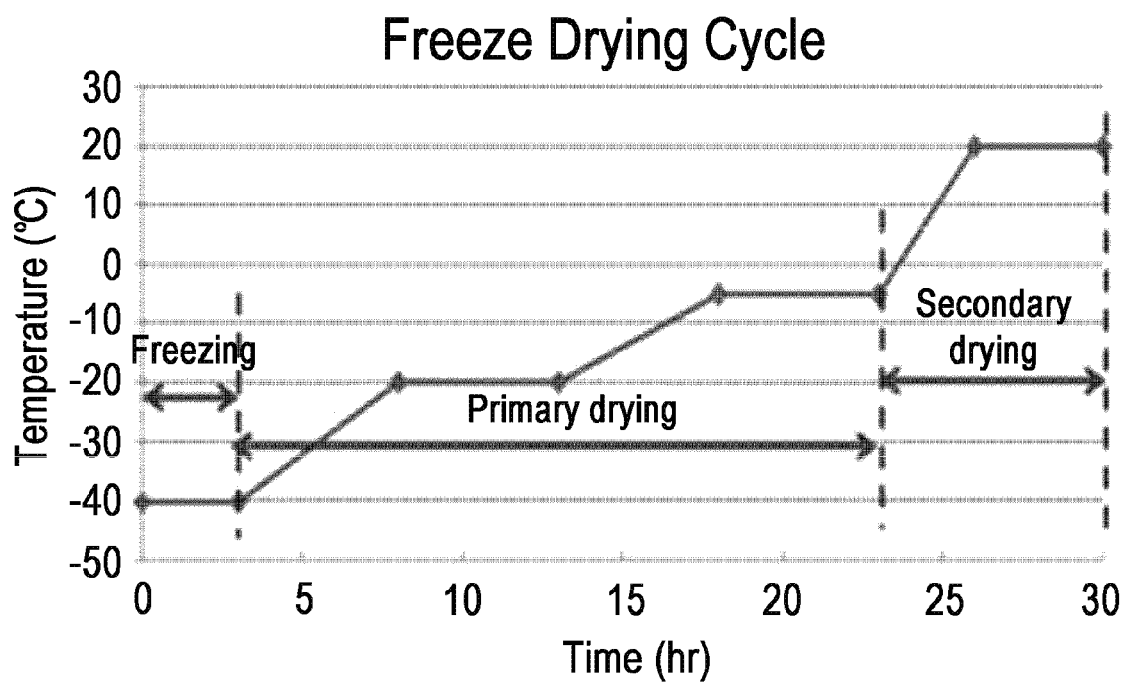

[Figure 3]
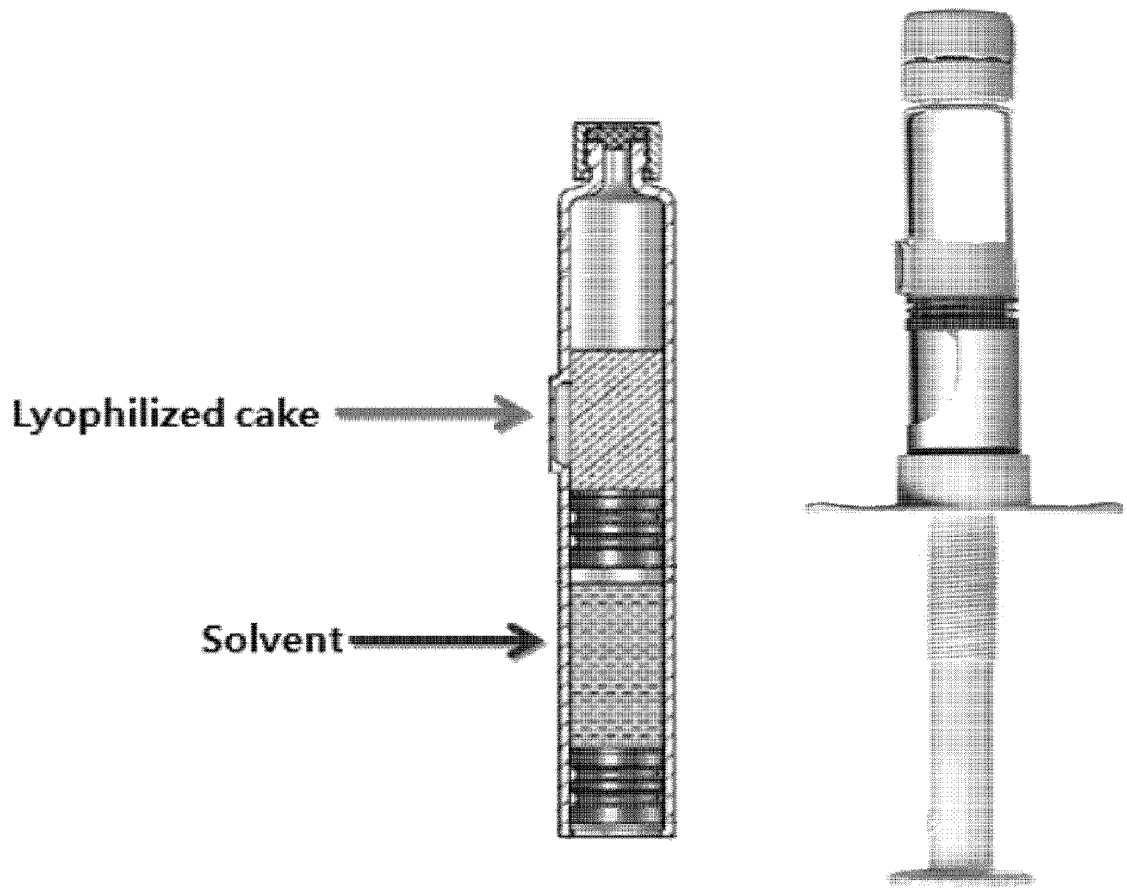

US 10,987,425 B2

LIQUID FORMULATION OF LONG-ACTING HUMAN GROWTH HORMONE IMMUNOGLOBULIN CONJUGATE

CROSS REFERENCE TO RELATED APPLICATIONS

This application is a National Stage of International Application No. PCT/KR2014/009059 filed Sep. 26, 2014, claiming priority based on Korean Patent Application No. 10-2013-0115177 filed Sep. 27, 2013.

TECHNICAL FIELD

The present invention relates to a formulation of a long-acting human growth hormone conjugate, comprising a long-acting human growth hormone (hGH) conjugate in which the human growth hormone as a physiologically active peptide is linked to an immunoglobulin Fc region, a buffer, a non-ionic surfactant and a sugar alcohol, specifically a lyophilized formulation and a liquid formulation of a long-acting human growth hormone conjugate, a method for preparing the lyophilized formulation, a method for reconstituting the lyophilized formulation and a kit comprising the lyophilized formulation and a solution for reconstitution.

BACKGROUND ART

Human growth hormone (hereinafter referred to as "hGH") is a polypeptide hormone consisting of 191 amino acids having a molecular weight of about 22,000, being secreted from the anterior pituitary gland. The human growth hormone has been mostly used for the treatment of pediatric pituitary dwarfism. Conventionally, hGH extracted from the human pituitary gland has been used but only a very limited number of people have been treated due to its limited supply. Also, since the reports of Creutzfeldt-Jacob disease, a degenerative neurological disorder, found in some of the patients treated with the hGH extracted from the pituitary gland, the use of hGH extracted from the pituitary glands has been banned. Currently, the development of genetic engineering techniques has enabled production of hGH in *E. coli* and yeast, and the biosynthetic hGH medicines produced therefrom have been approved in several countries since 1985 and become commercially available after passing toxicological and clinical tests.

In general, polypeptides such as hGH have low stability and thus are easily denatured. Also, they are readily degraded by serum proteases and removed by the kidneys or liver. Thus, protein drugs containing polypeptides as pharmaceutical ingredient have to be frequently administered to patients to maintain its blood concentration and titer. However, since the protein drugs are often administered in the form of injection, frequent injection of the protein drugs to maintain the optimal blood concentration of the active polypeptides causes a lot of pain to the patients. To solve these problems, there have been many attempts to increase the stability of a protein drug in blood and maintain its blood concentration at high level for a long period of time to maximize the therapeutic effects of the medicine.

Recently, Korean Patent No. 10-0567902 (Physiologically Active Polypeptide Conjugate Having Improved In Vivo Durability) and Korean Patent No. 10-0725315 (Protein Complex Using An Immunoglobulin Fragment And Method For The Preparation Thereof) disclosed conjugates prepared by linking physiologically active polypeptides with an immunoglobulin Fc region and a non-peptidyl polymer, as long-acting formulations of protein drugs, enabling both a minimal reduction of protein activity and an increase in protein stability. According to these methods, hGH may be used as a physiologically active polypeptide to prepare a long-acting hGH conjugate. For commercializing the drug containing the long-acting hGH conjugate, it is essential to prevent physicochemical changes such as denaturation, aggregation, adsorption, or hydrolysis due to degradation induced by light, heat or impurities in additives during storage and transport processes, while retaining the in-vivo activities of hGH. Since the long-acting hGH conjugate has a larger size and increased molecular weight compared to a hGH polypeptide, it is difficult to stabilize the conjugate.

Lyophilization (freeze-drying) is commonly used to preserve proteins by removing water from the protein preparation of interest. Lyophilization is a process by which the material to be dried is first frozen and then the ice or frozen solvent is removed by sublimation. An excipient may be included in a pre-lyophilized formulation to maintain or enhance protein stability during the lyophilization process or to improve stability of the lyophilized product during storage. However, the composition of a lyophilized formulation applicable to one protein is often not applicable to other proteins due to the difference in properties of the proteins to be preserved. Specifically, different proteins may be inactivated under different conditions during the storage, lyophilization and reconstitution processes owing to their different chemical properties. That is, the enhancement in stability provided by the materials used for stabilization is not identical for different proteins and, accordingly, the suitable ratios, concentrations and kinds of the stabilizers used to provide stability during the storage, lyophilization and reconstitution processes vary depending on the physicochemical properties of the proteins. When different stabilizers are used in combination, an unwanted negative effect may be derived due to their competition or adverse reactions and an unexpected effect may occur due to the change in the nature or concentration of the protein during the lyophilization or storage processes. Therefore, protein stabilization requires a lot of effort and precautions.

Particularly, since a long-acting hGH conjugate having improved in vivo durability and stability has a form in which the human growth hormone as a physiologically active peptide is linked to the immunoglobulin Fc region, its molecular weight and volume differs greatly from those of the human growth hormone. Therefore, a special composition is required for stabilizing the protein. Also, since each of the physiologically active peptide hGH and the immunoglobulin Fc region has different physicochemical properties, they should be stabilized simultaneously. However, as described above, different peptides or proteins may be gradually inactivated under different ratios and conditions due to the difference in their physicochemical properties. Also, when stabilizers suitable for each peptide or protein are used simultaneously, they may cause adverse results due to competitive interactions between them and side effects. Furthermore, as the properties and concentration of the stored protein may change during its storage, the stabilizers may exhibit unexpected side effects. Therefore, for a long-acting hGH conjugate, it is difficult to find a composition suitable for a stabilizer capable of stabilizing both the physiologically active peptide hGH and the immunoglobulin Fc region simultaneously. In addition, for a lyophilized formulation, the methods of lyophilization and reconstituting should be controlled in various ways to maintain protein stability and activity upon reconstitution. These methods may also vary depending on the composition of the formulation and the protein used thereof.

Additionally, when a lyophilized formulation comprises a protein at high concentration, the protein may aggregate during lyophilization because of the high concentration, and its handling also becomes difficult. Therefore, a protein at high concentration had been conventionally obtained by preparing a lyophilized formulation comprising the protein at low concentration and then reconstituting it with a small volume instead of performing lyophilization followed by reconstitution of the high-concentration protein. However, if the protein is reconstituted with a small volume, not only the protein but also other ingredients included therein become too concentrated and too hypertonic for the formulation to be directly applicable to patients. Accordingly, there is a need for the development of a formulation that allows lyophilizing of the high-concentration protein as it is.

Recently, formulations of proteins and peptides that can be used repeatedly for the patients' convenience have been developed. However, these multi-use formulations should contain a preservative to prevent microbial contamination after repeated administration and prior to disposal. The multi-use formulation containing a preservative has a few advantages over a single-use formulation. For example, as for the single-use formulation, a large amount of drug may be wasted depending on the dosage, which may be reduced when the multi-use formulation is used. Furthermore, the multi-use formulation can be used several times without the concern about microbial growth during a given time period and, since it can be supplied in a single container, packaging can be minimized, leading to economic benefits. However, use of the preservative may affect the protein stability. The most well-known problem associated with the use of a preservative is formation of precipitates. Precipitation of the protein may reduce the therapeutic effect of the drug and induce an unexpected immune response when administered to the body. Therefore, it is critical to select an appropriate type and concentration of the preservative that maintain the ability of microbial contamination without affecting the protein stability.

In general, a formulation in solution state is developed in a syringe form. The most commonly-used type is a prefilled syringe, and a more convenient autoinjector is also frequently used. In addition, a pen injector which allows automated injection of a required dosage to a patient is used mainly for growth hormone, insulin, etc. Although these injection devices are convenient for administration of formulations in solution state, they cannot be used for the drugs which must be lyophilized because of low stability.

In general, a lyophilized formulation is prepared in a reinforced glass vial separately from a solvent for dissolution. The two are mixed to dissolve the lyophilized formulation immediately prior to injection using a syringe. The recent trend is from a lyophilized vial (e.g., a reinforced glass vial) toward a single-use or multi-use syringe for the patients' convenience. Examples include the dual chamber cartridge of Vetter (Germany).

DISCLOSURE

Technical Problem

Under this background, the inventors of the present invention have made efforts to develop a lyophilized formulation capable of maintaining the stability of a long-acting human growth hormone conjugate during the lyophilization process and capable of storing it for a long period of time and a liquid formulation capable of stably storing a long-acting human growth hormone conjugate. As a result, they have found that when a stabilizer comprising a buffer, a sugar alcohol and a non-ionic surfactant is used, the stability of a long-acting hGH conjugate is increased during lyophilization and storage, and thus a cost-effective and stable liquid formulation could be prepared. Also, it was confirmed that when the concentration of the long-acting hGH conjugate is 10-58.5 mg/mL, a sodium chloride-free liquid formulation with superior stability can be provided. Furthermore, it was confirmed that the lyophilized formulation of the present invention is not only stable during storage and transportation but also it has appropriate osmotic pressure and stability for subcutaneous injection when reconstituted. In addition, it was confirmed that the lyophilized formulation can be used as a multi-use formulation since it maintains stability even when a preservative is included.

Technical Solution

The present invention is directed to providing a formulation of a long-acting human growth hormone conjugate, comprising a long-acting human growth hormone (hGH) conjugate in which the human growth hormone (hGH) as a physiologically active peptide is linked to an immunoglobulin Fc region, a buffer, a non-ionic surfactant and a sugar alcohol.

The present invention is also directed to providing a lyophilized formulation of a long-acting hGH conjugate, comprising a lyophilized mixture of an aqueous solution comprising a long-acting human growth hormone conjugate in which the hGH as a physiologically active peptide is linked to an immunoglobulin Fc region and an albumin-free solution comprising a buffer, a non-ionic surfactant and a sugar alcohol.

The present invention is also directed to providing a liquid formulation of a long-acting hGH conjugate, comprising a pharmaceutically effective amount of a long-acting hGH conjugate in which the hGH as a physiologically active peptide is linked to an immunoglobulin Fc region and an albumin-free stabilizer, wherein the stabilizer comprises a buffer, a non-ionic surfactant and a sugar alcohol.

The present invention is also directed to providing a method for preparing the formulations.

The present invention is also directed to providing a method for reconstituting the lyophilized formulation, comprising adding a solution for reconstitution to the lyophilized mixture of an aqueous solution comprising a long-acting human growth hormone conjugate in which the human growth hormone as a physiologically active peptide is linked to an immunoglobulin Fc region and an albumin-free solution comprising a buffer, a non-ionic surfactant and a sugar alcohol.

The present invention is also directed to providing a kit comprising the lyophilized formulation of a long-acting hGH conjugate.

Advantageous Effects

Since the formulation of a long-acting hGH conjugate of the present invention does not comprises human serum albumin or any potentially hazardous factors, there is no concern of viral contamination. In addition, the formulation allows for a high stability of the long-acting hGH conjugate which is prepared by linking the hGH polypeptide to the immunoglobulin Fc region, thus having a larger molecular weight when compared to a wild-type and increased in vivo durability. In particular, the lyophilized formulation provides superior stability not only during lyophilization but also after reconstitution, and also maintains stability even when it contains a preservative, thus being useful as a formulation for multiple administrations.

DESCRIPTION OF DRAWINGS

FIG. 1 shows a temperature gradient used in a lyophilization process of the present invention.

FIG. 2 shows a temperature gradient used in a lyophilization process of the present invention wherein primary drying is divided into two stages.

FIG. 3 shows a Vetter's dual chamber cartridge.

BEST MODE

In an aspect, the present invention provides a formulation of a long-acting human growth hormone conjugate, comprising a long-acting human growth hormone (hGH) conjugate in which the human growth hormone (hGH) as a physiologically active peptide is linked to an immunoglobulin Fc region, a buffer, a non-ionic surfactant and a sugar alcohol.

In another aspect, the present invention provides a lyophilized formulation of a long-acting human growth hormone conjugate, comprising a lyophilized mixture of an aqueous solution comprising a long-acting hGH conjugate in which the hGH as a physiologically active peptide is linked to an immunoglobulin Fc region and an albumin-free solution comprising a buffer, a non-ionic surfactant and a sugar alcohol.

In an exemplary embodiment, the buffer is an acetate buffer, a histidine buffer or a citrate buffer.

In another exemplary embodiment, the buffer is an acetate buffer.

In another exemplary embodiment, the acetate is sodium acetate and the citrate is sodium citrate.

In another exemplary embodiment, the pH of the buffer ranges from 5.0 to 6.0.

In another exemplary embodiment, the sugar alcohol is mannitol or sorbitol.

In another exemplary embodiment, the sugar alcohol is included with a concentration ranging from 1% (w/v) to 10% (w/v) of the total volume of the aqueous solution.

In another exemplary embodiment, the sugar alcohol is included with a concentration ranging from 2.5% (w/v) to 5% (w/v).

In another exemplary embodiment, the non-ionic surfactant is polysorbate 80.

In another exemplary embodiment, the concentration of the non-ionic surfactant ranges from 0.001% (w/v) to 0.05% (w/v) of the total volume of the aqueous solution.

In another exemplary embodiment, the albumin-free solution further comprises at least one selected from the group consisting of a sugar, a polyhydric alcohol and an amino acid.

In another exemplary embodiment, the amino acid is histidine or glycine.

In another exemplary embodiment, the concentration of the histidine ranges from 1 to 10 mM.

In another exemplary embodiment, the concentration of the long-acting hGH conjugate ranges from 10 to 100 mg/mL.

In another exemplary embodiment, the albumin-free solution further comprises an isotonic agent.

In another exemplary embodiment, the isotonic agent is sodium chloride.

In another exemplary embodiment, the concentration of the sodium chloride ranges from 0 to 200 mM.

In another exemplary embodiment, a container of the lyophilized formulation is a vial, a dual chamber cartridge or a dual chamber syringe.

In another aspect, the present invention provides a liquid formulation of a long-acting hGH conjugate, comprising a pharmaceutically effective amount of a long-acting hGH conjugate in which the hGH as a physiologically active peptide is linked to an immunoglobulin Fc region and an albumin-free stabilizer, wherein the stabilizer comprises a buffer, a non-ionic surfactant and a sugar alcohol.

In an exemplary embodiment, the liquid formulation does not comprise an isotonic agent.

In another exemplary embodiment, the buffer is a citrate buffer, an acetate buffer or a histidine buffer.

In another exemplary embodiment, the sugar alcohol is mannitol or sorbitol.

In another exemplary embodiment, the sugar alcohol is included with a concentration ranging from 2% (w/v) to 4.5% (w/v).

In another exemplary embodiment, the sugar alcohol is included with a concentration of 4% (w/v).

In another exemplary embodiment, the pH of the buffer ranges from 5.0 to 6.0.

In another exemplary embodiment, the pH of the buffer is 5.2.

In another exemplary embodiment, the non-ionic surfactant is polysorbate 80.

In another exemplary embodiment, the concentration of the non-ionic surfactant ranges from 0.001% (w/v) to 0.05% (w/v) of the total volume of the formulation.

In another exemplary embodiment, the long-acting hGH conjugate is included in the formulation with a concentration ranging from 5.0 mg/mL to 60.0 mg/mL.

In another exemplary embodiment, the hGH has the same amino acid sequence as that of the wild-type hGH.

In another exemplary embodiment, the immunoglobulin Fc region is an Fc region derived from IgG, IgA, IgD, IgE or IgM.

In another exemplary embodiment, each domain of the immunoglobulin Fc region is a hybrid of domains with different origin derived from an immunoglobulin selected from the group consisting of IgG, IgA, IgD, IgE and IgM.

In another exemplary embodiment, the immunoglobulin Fc region is a dimer or a multimer composed of a single-chain immunoglobulin consisting of domains with the same origin.

In another exemplary embodiment, the immunoglobulin Fc region is an IgG4 Fc region.

In another exemplary embodiment, the immunoglobulin Fc region is an aglycosylated human IgG4 Fc region.

In another exemplary embodiment, the conjugate is in such a form that the hGH is linked to the immunoglobulin Fc via a non-peptidyl polymer as a linker or via genetic recombination.

In another exemplary embodiment, the non-peptidyl polymer is selected from the group consisting of a biodegradable polymer such as polyethylene glycol, polypropylene glycol, a copolymer of ethylene glycol and propylene glycol, a polyoxyethylated polyol, polyvinyl alcohol, a polysaccharide, dextran, polyvinyl ethyl ether, polylactic acid (PLA) and polylactic-glycolic acid (PLGA), a lipid polymer, chitin, hyaluronic acid and a combination thereof.

In another exemplary embodiment, the non-peptidyl polymer is polyethylene glycol.

In another exemplary embodiment, the formulation is for the treatment of pituitary dwarfism, growth hormone deficiency, Prader-Willi syndrome or idiopathic short stature.

In another aspect, the present invention provides a lyophilized formulation of a long-acting hGHconjugate, comprising a lyophilized mixture of an aqueous solution comprising a long-acting hGH conjugate in which the hGH as a physiologically active peptide is linked to an immunoglobulin Fc region and an albumin-free solution comprising an acetate buffer, polysorbate 80 and mannitol.

In another aspect, the present invention provides a liquid formulation of a long-acting hGHconjugate, comprising a pharmaceutically effective amount of a long-acting hGH conjugate in which the hGHas a physiologically active peptide is linked to an immunoglobulin Fc region and an albumin-free stabilizer comprising a citrate buffer, polysorbate 80 and mannitol, the stabilizer not comprising an isotonic agent.

In another aspect, the present invention provides a method for preparing the lyophilized formulation, comprising lyophilizing a long-acting hGH conjugate in which the human growth hormone as a physiologically active peptide is linked to an immunoglobulin Fc region and an albumin-free solution comprising a buffer, a non-ionic surfactant and a sugar alcohol.

In another aspect, the present invention provides a method for reconstituting the lyophilized formulation, comprising adding a solution for reconstitution to the lyophilized mixture of an aqueous solution comprising a long-acting hGH conjugate in which the human growth hormone (hGH) as a physiologically active peptide is linked to an immunoglobulin Fc region and an albumin-free solution comprising a buffer, a non-ionic surfactant and a sugar alcohol included in the lyophilized formulation.

In an exemplary embodiment, the solution for reconstitution is water for injection.

In another exemplary embodiment, the solution for reconstitution further comprises a preservative.

In another exemplary embodiment, the preservative is benzyl alcohol, m-cresol or phenol.

In another exemplary embodiment, the formulation reconstituted by the method comprises the long-acting hGH conjugate with a concentration ranging from 10 to 100 mg/mL.

In another aspect, the present invention provides a kit comprising the lyophilized formulation of a long-acting hGH conjugate.

MODE FOR INVENTION

In an aspect, the present invention provides a formulation of a long-acting human growth hormone conjugate, comprising a long-acting human growth hormone (hGH) conjugate in which the hGH as a physiologically active peptide is linked to an immunoglobulin Fc region, a buffer, a non-ionic surfactant and a sugar alcohol.

As used herein, the term "long-acting human growth hormone (hGH) conjugate" refers to a conjugate in which the physiologically active peptide human growth hormone is linked to an immunoglobulin Fc region and the physiological activity of which has an increased in vivo duration when compared to a wild-type hGH. The term "long-acting" as used herein means that the physiological activity has a longer duration than a wild-type hGH. As used herein, the term "conjugate" refers to a form in which the human growth hormone is coupled to an immunoglobulin Fc region.

Specifically, the formulation may be a lyophilized formulation of a long-acting hGH conjugate, comprising a lyophilized mixture of an aqueous solution comprising a long-acting hGH conjugate in which the hGH as a physiologically active peptide is linked to an immunoglobulin Fc region and an albumin-free solution comprising a buffer, a non-ionic surfactant and a sugar alcohol.

As used herein, the term "lyophilized formulation of a long-acting hGH conjugate" refers to a lyophilized formulation comprising a long-acting hGH conjugate. It includes a formulation comprising materials existing in solid state, obtained by lyophilizing a long-acting hGH conjugate and a substance to stabilize the same such as an excipient. In the present invention, the lyophilized formulation includes the lyophilized substance itself. The lyophilized substance may also be referred to as a lyophilized cake.

The lyophilized formulation is prepared by a lyophilization process of sublimating water from a preparatory formulation comprising a long-acting hGH conjugate and an excipient for stabilizing the long-acting hGH conjugate. In the present invention, the lyophilized formulation of a long-acting hGH conjugate may comprise a therapeutically effective amount of a long-acting hGH conjugate and a therapeutically effective amount of the hGH may be contained in a single-use container or a multi-use container, although being not limited thereto.

The lyophilized formulation may be contained in a vial (e.g., a reinforced glass vial), a dual chamber cartridge or a dual chamber syringe, although being not limited thereto.

The lyophilized formulation of the present invention has a composition capable of stabilizing the long-acting hGH conjugate during a lyophilization process and capable of maintaining the stability of the formulation when it is reconstituted after storage. In particular, the lyophilized formulation of the present invention is capable of providing stability even when the long-acting hGH conjugate is included with a high concentration ranging from 10 mg/mL to 100 mg/mL.

The lyophilized formulation of a long-acting hGH conjugate may be stored in a container and reconstituted when administration to a subject is necessary.

As used herein, the term "reconstitution" means that the lyophilized substance in solid state liquefied to allow for administration of the hGH conjugate. The concentration of the long-acting hGH conjugate included in the lyophilized formulation of the present invention ranges from 1 mg/mL to 150 mg/mL, specifically from 10 mg/mL to 120 mg/mL, more specifically from 10 mg/mL to 100 mg/mL, upon reconstitution, although not being limited thereto.

The reconstitution may be conducted by dissolving the lyophilized substance by adding a solvent to a vial containing the lyophilized substance or by adding a solvent to the lyophilized substance contained in a single-use syringe or a multi-use syringe, but is not specially limited thereto.

The lyophilized formulation of a long-acting hGH conjugate of the present invention is advantageous over the existing liquid formulation in that the hGH conjugate can be stably stored and the effective concentration of the conjugate can be controlled. The concentration after the reconstitution may be identical to or different from the concentration of the pre-lyophilized formulation during the lyophilization process.

The lyophilized formulation of the present invention comprises a lyophilized mixture of an aqueous solution comprising a long-acting hGHconjugate and an albumin-free solution comprising a buffer, a non-ionic surfactant and a sugar alcohol.

As used herein, the term "albumin-free solution" refers to a substance which is capable of allowing the long-acting hGH conjugate to be stably stored and maintain its stability during lyophilizing and reconstitution processes. In particular, the albumin-free solution refers to an aqueous solution which comprises a long-acting hGH conjugate and an excipient stabilizing the same and, thus, provides stability of the long-acting hGH conjugate during a lyophilization process and allows the preparation of a lyophilized formulation having storage stability. Specifically, the aqueous solution comprises a buffer, a sugar alcohol and a non-ionic surfactant. Further, an isotonic agent may be included for adjustment of osmotic pressure. For proteins such as the long-acting hGH conjugate, storage stability is important not only to ensure an accurate administration dosage but also to suppress the potential formation of antigenic substances against the long-acting hGH conjugate. In the present invention, the term albumin-free solution may be used interchangeably with a "preformulation".

Since the concentration of the long-acting hGH conjugate can be controlled by adjusting the volume of the solution for reconstitution added to the lyophilized formulation, the concentration of the long-acting hGH conjugate in the albumin-free solution is not particularly limited. However, the formulation of the present invention is advantageous in that even an albumin-free solution comprising the long-acting hGH conjugate with a high concentration of 10-100 mg/mL or above can be stably lyophilized, the prepared lyophilized formulation can be quickly dissolved within 3 minutes and the stability of the long-acting hGH conjugate can be maintained in the reconstituted solution.

The aqueous solution does not contain human serum albumin. Since the human serum albumin that can be used as a protein stabilizer is produced from human serum, there is a risk of contamination by pathogenic viruses derived from human. In addition, gelatin or bovine serum albumin may cause diseases or may induce an allergic response in some patients. Since the albumin-free solution of the present invention proteins does not contain heterologous proteins such as serum albumin derived from human or animal or purified gelatin, there is no risk of viral infection.

As used herein, the term "buffer" refers to a solution that is comprised in the albumin-free solution of the present invention and works to maintain a stable pH level of the formulation after a lyophilization or reconstitution process such that a sharp change in pH of the formulation is prevented to keep the activity of the long-acting hGH conjugate stable. The buffer may include an alkaline salt (e.g., sodium or potassium phosphate, or monobasic or dibasic salts thereof), a citrate (e.g., sodium citrate or citric acid), an acetate (e.g., sodium acetate or acetic acid), histidine, any other pharmaceutically acceptable pH buffering agent known in the art, or a combination thereof. The buffer may be specifically an acetate buffer, a histidine buffer or a citrate buffer, more specifically an acetate buffer or a citrate buffer, although not being limited thereto.

The concentration of the citrate or acetate that constitutes the buffer is specifically in a range from 5 to 100 mM, more specifically in a range from 10 to 50 mM, although not being limited thereto. The pH of the buffer is specifically in a range from 4.0 to 7.0, more specifically in a range from 5.0 to 6.0, further more specifically in a range from 5.2 to 6.0, although not being limited thereto.

As used herein, the term "sugar alcohol" refers to a hydrogenated carbohydrate that is comprised in the lyophilized formulation of the present invention and works to protect the protein of the long-acting hGH conjugate during a lyophilization process and to improve the stability of the long-acting hGH conjugate after reconstitution. The concentration of the sugar alcohol used in the present invention may be in a range from 1 to 10% (w/v) of the total volume of the formulation, although not being limited thereto. Specifically, the concentration of the sugar alcohol may be in a range from 2.5 to 5% (w/v). When the concentration of the sugar alcohol is within this range, a reconstituted formulation obtained by reconstitution using a solution for reconstitution of the same volume as that of the preformulation may have an osmotic pressure corresponding to that of an isotonic solution, although not being limited thereto.

The sugar alcohol used in the present invention may be at least one selected from the group consisting of mannitol and sorbitol, specifically mannitol, but is not specially limited thereto. Being included in the formulation of the present invention, the sugar alcohol such as mannitol may serve to adjust osmotic pressure. Specifically, the formulation obtained by reconstituting the lyophilized formulation of the present invention may be isotonic. However, it a hypertonic or hypotonic formulation is also suitable in the present invention.

As used herein, the term "non-ionic surfactant" refers to a substance that reduces the surface tension of a protein solution to prevent the protein from being adsorbed onto a hydrophobic surface or from aggregating after reconstitution. Specific examples of the non-ionic surfactant that can be used in the present invention include a polysorbate-type non-ionic surfactant, a poloxamer-type non-ionic surfactant and a combination thereof. More specifically, a polysorbate-type non-ionic surfactant may be used. Examples of the polysorbate-type non-ionic surfactant include polysorbate 20, polysorbate 40, polysorbate 60 and polysorbate 80, and among them polysorbate 80 is preferred, although not being limited thereto. It may not be appropriate to add the non-ionic surfactant at a high concentration to the formulation, since a non-ionic surfactant at high concentration can cause interference effects when protein is analyzed to determine protein concentration or stability through analytic methods such as UV-spectrometric method or isoelectric focusing (IEF) and thus make it hard to determine the protein stability accurately. Therefore, the lyophilized formulation of the present invention may comprise the non-ionic surfactant specifically at a low concentration of 0.1% (w/v) or less, more specifically in a range from 0.001 to 0.1% (w/v), and further more specifically in a range from 0.001 to 0.05% (w/v), although not being limited thereto.

Specifically, the albumin-free solution may further comprise at least one selected from the group consisting of a sugar, a polyhydric alcohol and an amino acid. It was confirmed by the inventors of the present invention that, when histidine is further added as the amino acid, dissolution rate can be improved and reconstitution can be achieved without foaming.

Specific examples of the sugar that can be further included to increase the storage stability of the long-acting hGH conjugate include monosaccharides such as mannose, glucose, fucose and xylose and polysaccharides such as lactose, maltose, sucrose, raffinose and dextran. Specific examples of the polyalcohol include propylene glycol, low-molecular-weight polyethylene glycol, glycerol, low-molecular-weight polypropylene glycol and a combination thereof. Examples of the amino acid include histidine or glycine, although not being limited thereto. The histidine, etc. may be present in the aqueous solution at a concentration ranging from 1 to 10 mM, although not being limited thereto.

The albumin-free solution may further comprise an isotonic agent for control of osmotic pressure.

As used herein, the term "isotonic agent" refers to an agent that maintains an appropriate osmotic pressure when the long-acting hGH conjugate is administered into the body after being reconstituted. The isotonic agent may have an effect of further stabilizing the long-acting hGH conjugate in solution. For example, the isotonic agent may be a water-soluble inorganic salt, specifically sodium chloride, although not being limited thereto. The concentration of sodium chloride used in the present invention is specifically in a range from 0 to 200 mM, although not being limited thereto. Also, depending on the type and amount of the substances comprised in the formulation, the amount of the isotonic agent included can be adjusted such that the solution formulation comprising all of the ingredients becomes isotonic.

The albumin-free solution may be lyophilized after being diluted ½-fold, ¼-fold or further. It was confirmed by the inventors of the present invention that dissolution time can be reduced when the albumin-free solution is lyophilized after being diluted ½-fold or ¼-fold (Test Example 1-(5)).

The lyophilized formulation of the present invention comprising the lyophilized mixture exhibits superior dissolution time. The dissolution time is one of important properties of a lyophilized substance. If the dissolution time is long, the protein has to be exposed to a concentrated solution for a long time, during which it can be denatured. Also, since the incompletely dissolved product cannot be administered, a short dissolution time can provide convenience for both the patients and the physicians. However, the dissolution time is inevitably increased as the protein concentration increases. Accordingly, development of a formulation with short dissolution time can be an important issue for a high-concentration lyophilized formulation.

It was confirmed by the inventors of the present invention that the lyophilized formulation of the present invention is dissolved within as short as 10 seconds and as long as 3 minutes even when it comprised the long-acting hGH conjugate at a high concentration of 10 mg/mL or above.

The desired dosage of a lyophilized product may be achieved by lyophilizing the target protein with a desired concentration and then reconstituting the same with a volume of a preformulation, although not being specially limited thereto. Alternatively, the preformulation may be lyophilized with an increased volume through dilution and then reconstituted using a solution for reconstitution with a smaller volume. However, if the preformulation is overly diluted, the lyophilization cycle (in particular, primary drying time) may be prolonged and thus production cost may be increased. Accordingly, the formulation of the present invention is also advantageous in terms of cost in that even the high-concentration long-acting hGH conjugate can be lyophilized without excessive dilution.

In addition, the lyophilized formulation of the present invention may further comprise other ingredients or materials that are known in the art in addition to the above-described buffer, isotonic agent, sugar alcohol, non-ionic surfactants and the preservative included in the solution for reconstitution, unless they do not diminish the effect of the present invention.

The inventors of the present invention prepared, as a preformulation, a lyophilized formulation comprising a long-acting hGH conjugate and an albumin-free solution comprising a buffer, a sugar alcohol and a surfactant and evaluated its stability and dissolution rate. Specifically, a long-acting hGH conjugate was lyophilized with a concentration of 19.5 mg/mL or 78.0 mg/mL using a pre-lyophilized formulation comprising a 20 mM citrate buffer of pH 5.2 or pH 5.6, 150 mM sodium chloride, 5% mannitol and 0.005% polysorbate 80 and then reconstituted using distilled water. Superior stability was superior at the above concentrations. In particular, the stability was better at the higher concentration of 78.0 mg/mL. Also, good stability was achieved at pH 5.2 and 5.6 both (Test Example 1-(1)). In addition, when a long-acting hGH conjugate was dissolved in a pre-lyophilized formulation comprising a 20 mM acetate buffer of pH 5.2 or pH 5.6, 150 mM NaCl, 5% mannitol and 0.005% polysorbate 80 and then reconstituted using a solution for reconstitution comprising m-cresol, benzyl alcohol or phenol as a preservative, the stability was maintained. This result confirms that a reconstituted formulation with preserved activity can be prepared by reconstituting a lyophilized substance with a solution for reconstitution comprising a preservative. In particular, when the aqueous acetate solution was used, superior stability could be achieved without precipitation even when the reconstitution was conducted using a solution for reconstitution comprising a preservative (Test Example 1-(2)). Furthermore, it was confirmed that the dissolution time of the prepared lyophilized formulation is increased as the concentration of the conjugate increases from 19.5 mg/mL to 39.0 mg/mL to 58.5 mg/mL and to 70.0 mg/mL (Test Example 1-(3)). In addition, superior dissolution time and stability were achieved even when the albumin-free solution did not contain a salt and the dissolution rate could be increased by increasing the concentration of mannitol. And, when histidine was added, it was possible to reduce the dissolution time without increasing the concentration of mannitol (Test Example 1-(4)). Further, the inventors found out that the dissolution rate is further improved when the preformulation is diluted to decrease density (Test Example 1-(5)) and established the optimized drying condition under which the lyophilized substance can be completely dried (Test Example 1-(6)). It was also demonstrated that the presence of mannitol greatly affects the dissolution time (Test Example 1-(7)) and that an isotonic osmotic pressure can be achieved with a dissolution time of 30 seconds or less when the mannitol is concentration 4-4.5% even for the high-concentration long-acting hGH conjugate of 58.5 mg/mL (Test Example 1-(8)). In addition, the stability was maintained nearly constant even after the prepared lyophilized formulations were stored at 4° C. or 25° C. for 6 months. Also, the stability was maintained even after the lyophilized formulations were stored at 25° C. for 2 weeks after reconstitution (Test Example 1-(9)).

Specifically, the formulation may be a liquid formulation of a long-acting hGH conjugate, comprising a long-acting hGH conjugate in which the hGH as a physiologically active peptide is linked to an immunoglobulin Fc region and an albumin-free stabilizer, wherein the stabilizer comprises a buffer, a non-ionic surfactant and a sugar alcohol.

The long-acting hGH conjugate is the same as described above.

As used herein, the term "liquid formulation of a long-acting hGH conjugate" refers to a liquid formulation which comprises a long-acting hGH conjugate. The liquid formulation includes liquid formulations for both internal and external application. In the present invention, the liquid formulation of a long-acting hGH conjugate may comprise a pharmaceutically effective amount of the long-acting hGH conjugate. In general, the pharmaceutically effective amount of hGH corresponds to about 1 to 3 mg in a single-use vial, but is not limited thereto.

And, the concentration of the long-acting hGH conjugate comprised in the liquid formulation of the present invention ranges specifically from 5.0 to 60.0 mg/mL, although not being limited thereto.

The liquid formulation of a long-acting hGH conjugate comprises a pharmaceutically effective amount of a long-acting hGH conjugate and an albumin-free stabilizer.

As used herein, the term "stabilizer" refers to a substance that allows the long-acting hGH conjugate to be stored stably. Specifically, the stabilizer comprises a buffer, a sugar alcohol and a non-ionic surfactant. With regard to proteins such as the long-acting hGH conjugate, the storage stability is important for ensuring dose accuracy and suppressing the formation of potential antigens against the long-acting hGH conjugate.

As used herein, the term "buffer" refers to a solution that is comprised in the stabilizer of the present invention and works to maintain a stable pH level of the formulation, thereby preventing a drastic change in pH to maintain the activity of the long-acting hGH conjugate stable. The description of the buffer stated above with regard to the lyophilized formulation also applies here.

The buffer may be a citrate buffer, an acetate buffer or a histidine buffer, specifically a citrate buffer, although not being limited thereto. The concentration of the salt that constitutes the buffer is specifically in a range from 5 to 100 mM, more specifically in a range from 10 to 50 mM, although not being limited thereto. The pH of the buffer is in a range from 4.0 to 7.0, more specifically in a range from 5.0 to 6.0, further more specifically in a range from 5.2 to 6.0, most specifically 5.2, although not being limited thereto.

As used herein, the term "sugar alcohol" refers to a hydrogenated carbohydrate that is comprised in the liquid formulation of the present invention and works to improve the stability of the long-acting hGH conjugate. The concentration of the sugar alcohol used in the present invention is specifically in a range from 1 to 10% (w/v) of a total volume of the formulation, and more specifically in a range from 2% (w/v) to 4.5% (w/v), further more specifically 4% (w/v), although not being limited thereto. The sugar alcohol used in the present invention may be at least one selected from the group consisting of mannitol and sorbitol, specifically mannitol, although not specially limited thereto.

As used herein, the term "non-ionic surfactant" refers to a substance that reduces the surface tension of a protein solution to prevent the protein from being adsorbed onto a hydrophobic surface or from aggregating. Specific examples of the non-ionic surfactant that can be used in the present invention are the same as described above.

The formulation of the present invention may be one not containing an isotonic agent.

The isotonic agent is the same as described above.

The inventors of the present invention found that a formulation comprising an aqueous acetate or citrate solution of pH 5.2 as a buffer and comprising 4% (w/v) mannitol but not comprising an isotonic agent exhibits superior stability. In particular, a formulation comprising an aqueous citrate solution of pH 5.2 as a buffer and comprising 4% (w/v) mannitol but not comprising an isotonic agent exhibited the highest stability at the long-acting hGH conjugate concentration of 10.0 mg/mL.

Specific examples of the sugar that can be further included to increase the storage stability of the long-acting hGH conjugate are the same as described above. In addition, the liquid formulation of the present invention may further comprise other ingredients or materials that are known in the art in addition to the above-described buffer, sugar alcohol and non-ionic surfactants, unless they do not diminish the effect of the present invention.

In particular, the liquid formulation of the present invention may further comprise a preservative.

It was found that a formulation of a long-acting hGH conjugate not containing an isotonic agent exhibits the best stability of the long-acting hGH conjugate in a buffer at pH 5.2 when it comprises 4% mannitol (w/v). In particular, the best stability was achieved at the long-acting hGH conjugate concentration of 10.0 mg/mL when an acetate buffer was used (Test Example 2).

The formulation of the present invention may be for the treatment of pituitary dwarfism, growth hormone deficiency, Prader-Willi syndrome or idiopathic short stature and may be injected into after reconstitution to treat the diseases.

Hereinafter, the long-acting hGH conjugate is described in detail.

As used herein, the term "human growth hormone (hGH)" refers to a peptide hormone that stimulates growth, cell reproduction and regeneration in humans. The information on the sequence of the hGH can be obtained from common database such as the NCBI GenBank. In addition, the scope of the hGH in the present invention includes a protein possessing an amino acid sequence having a sequence homology of 70% or higher, specifically 80% or higher, more specifically 90% or higher, even more specifically 95% or higher, and most specifically 98% or higher to an amino acid sequence of a wild-type hGH, as long as it has a hGH activity. Also, as long as its biological activity is not significantly changed, any mutant derived from a wild-type hGH by substitution, deletion, or insertion of amino acid residues may be used in the present invention.

The hGH useful in the present invention may have an amino acid sequence of a wild-type hGH, its variant, its derivative, or fragments thereof.

As used herein, the term "hGH variant" refers to a peptide having at least one amino acid sequences different from those of the wild-type hGH while demonstrating the hGH activity. The hGH variant may be prepared by substitution, addition, deletion, or modification of some amino acids of the wild-type hGH or a combination thereof.

As used herein, the term "hGH derivative" refers to a peptide having at least 80% amino acid sequence homology to the wild-type hGH and exhibiting the hGH activity, in which some groups of the amino acid residues are chemically substituted (e.g., alpha-methylation, alpha-hydroxylation), deleted (e.g., deamination), or modified (e.g., N-methylation).

As used herein, the term "hGH fragment" refers to a peptide in which at least one amino acids are added or deleted at the N-terminal or the C-terminal of the hGH while retaining the hGH activity. The added amino acid be one which does not naturally occur (for example, D-amino acid).

In addition, the hGH used in the present invention may be obtained from a native or recombinant protein. Specifically, it is the recombinant hGH prepared by using *E. coli* as a host cell, although not being limited thereto.

As used herein, the term "immunoglobulin Fc region" refers to a part of immunoglobulin excluding the variable regions of the heavy chain and light chain, the heavy-chain constant region 1 ($C_H1$) and the light-chain constant region 1 ($C_L1$) of the immunoglobulin. The immunoglobulin Fc region may be the heavy-chain constant region 2 ($C_H2$) and the heavy-chain constant region 3 ($C_H3$) of an immunoglobulin, and may further comprise a hinge region at the heavy-chain constant region, although not being limited thereto. Also, the immunoglobulin Fc region of the present invention may be an extended Fc region that comprises a portion or full of the heavy-chain constant region 1 ($C_H1$) and/or the light-chain constant region 1 ($C_L1$) except for the variable regions of the heavy chain and light chain of immunoglobulin, as long as it has substantially the same or improved effect as compared to the wild-type protein. Also, the immunoglobulin Fc region may be a fragment wherein a considerably long portion of the amino acid sequence corresponding to $C_H2$ and/or $C_H3$ is deleted. That is, the immunoglobulin Fc region of the present invention may comprise 1) a $C_H1$ domain, a $C_H2$ domain, a $C_H3$ domain and a $C_H4$ domain, 2) a $C_H1$ domain and a $C_H2$ domain, 3) a $C_H1$ domain and a $C_H3$ domain, 4) a $C_H2$ domain and a $C_H3$ domain, 5) a combination of at least one domains and an immunoglobulin hinge region (or a portion of the hinge region), and 6) a dimer of a domain of the heavy-chain constant regions and a light-chain constant region, although not being limited thereto.

The immunoglobulin Fc region of the present invention comprises a native amino acid sequence and an amino acid sequence derivative (mutant) thereof. The amino acid sequence derivative refers to the sequence having different sequence from the native sequence by deletion, insertion, non-conservative or conservative substitution of at least one amino acid residues of the native amino acid sequence, or combinations thereof. For example, in IgG Fc, amino acid residues at positions 214 to 238, 297 to 299, 318 to 322, or 327 to 331 which are known to be important for protein binding may be suitable targets for modification.

Also, other types of derivatives may be used including the derivatives wherein a region capable of forming a disulfide bond is deleted, few amino acid residues at the N-terminal of a native Fc are eliminated, or a methionine residue is added at the N-terminal of the native Fc. Further, in order to eliminate the function of effector, a complement-binding site, for example C1q-binding site or antibody dependent cell mediated cytotoxicity (ADCC) site, may be deleted. Techniques for preparing such sequence derivatives of the immunoglobulin Fc region are disclosed in WO 97/34631 and WO 96/32478.

Substitution of amino acids in proteins and peptides, which do not change the overall protein activities, are known in the art (H. Neurath, R. L. Hill, The Proteins, Academic Press, New York, 1979). The most-commonly occurring exchanges are Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu and Asp/Gly, in both directions. In some cases, the Fc region may be modified by phosphorylation, sulfation, acrylation, glycosylation, methylation, farnesylation, acetylation, amidation, and the like. The aforementioned Fc derivatives demonstrate the same biological activity as the Fc region of the present invention, and they have an enhanced structural stability against heat, pH, and the like.

In addition, these Fc regions may be obtained from native proteins isolated from humans or other animals including cows, goats, swine, mice, rabbits, hamsters, rats and guinea pigs, or may be recombinants obtained from transformed animal cells or microorganisms or derivatives thereof. Here, the method of obtaining Fc regions from native immunoglobulin may include isolating the whole immunoglobulins from human or animal bodies and treating them with a protease. When papain is used for digesting immunoglobulins, they are cleaved into Fab and Fc regions, and when pepsin is used, the immunoglobulin is cleaved into pF'c and F(ab)$_2$. These fragments may be separated by size exclusion chromatography to isolate Fc or pF'c. Specifically, a human-derived Fc region is a recombinant immunoglobulin Fc region obtained from a microorganism.

In addition, the immunoglobulin Fc region of the present invention may be in a form of native sugar chains, longer sugar chains than native form, shorter sugar chains than native form, or a deglycosylated form. The extension or removal of the immunoglobulin Fc sugar chains may be done by using common methods in the art including chemical methods, enzymatic methods, and gene engineering method using a microorganism. The removal of sugar chains from an immunoglobulin Fc region results in a drastic decrease in its binding affinity to C1q of the first complement component C1 and thus antibody-dependent cell-mediated cytotoxicity or complement-dependent cytotoxicity is reduced or removed, and the occurrence of unnecessary immune responses in vivo can be avoided. In this regard, a deglycosylated or aglycosylated immunoglobulin Fc region is more preferable form as a drug carrier for the object of the present invention.

In addition, the immunoglobulin Fc region may be one derived from IgG, IgA, IgD, IgE and IgM, or those prepared by a combination or hybrid thereof. Specifically, it is derived from IgG or IgM, which are among the most abundant proteins in human blood, and most specifically from IgG, which is known to enhance the half-life of a ligand-binding protein. The immunoglobulin Fc may be generated by treating a native IgG with a certain protease, or by transformed cells using the genetic recombination technique. Specifically, the immunoglobulin Fc is a recombinant human immunoglobulin Fc produced in *E. coli*.

Meanwhile, the term "combination", as used herein, refers to a conjugation between a polypeptide encoding single-chain immunoglobulin Fc regions of the same origin and a single-chain polypeptide of different origin when forming a dimer or multimer. That is, a dimer or multimer can be formed from two or more fragments selected from the group consisting of IgG Fc, IgA Fc, IgM Fc, IgD Fc and IgE Fc fragments.

As used herein, the term "hybrid" refers to the presence of at least two sequences corresponding to immunoglobulin Fc fragments of different origins in a single-chain immunoglobulin Fc region. In the present invention, various types of hybrids may be used. That is, a hybrid of domains may be composed of one to four domains selected from the group consisting of $C_H1$, $C_H2$, $C_H3$ and $C_H4$ of IgG Fc, IgM Fc, IgA Fc, IgE Fc and IgD Fc, and may comprise a hinge region.

Meanwhile, IgG may also be divided into subclasses, IgG1, IgG2, IgG3 and IgG4, and a combination or hybrid thereof is also possible in the present invention, specifically IgG2 and IgG4 subclasses, and most specifically Fc region of IgG4 that lacks an effector function such as complement-dependent cytotoxicity. In other words, the most preferable immunoglobulin Fc region of the conjugate in the present invention is a human IgG4-derived non-glycosylated Fc region. The human-derived Fc region is preferred to a non-human derived Fc region which can act as an antigen in human body and cause undesirable immune responses such as production of new antibodies against the antigen.

The long-acting hGH conjugate of the present invention can be prepared by combining a hGH prepared from a native or recombinant form by any method and an immunoglobulin Fc region prepared by treating a wild-type IgG with a certain protease or produced from a transformed cell by using the recombination technique.

As a combining method used for this purpose, the conjugate can be prepared by cross-linking the hGH and the immunoglobulin Fc region using a non-peptidyl polymer or can be produced as a fusion protein wherein the hGH and the immunoglobulin Fc region are linked using the recombination technique. That is, the conjugate can be produced in a form where the hGH and the immunoglobulin Fc are linked via a non-peptidyl linker, or in a form of a fusion protein of the hGH and the immunoglobulin Fc. The fusion protein comprises a form where the hGH and the immunoglobulin Fc are combined via a peptidyl linker, although not being limited thereto.

As used herein, the term "non-peptidyl polymer" refers to a biocompatible polymer in which two or more repeating units are combined and the repeating units are connected to each other by any covalent bonding except for peptide bonding. In the present invention, the term non-peptidyl polymer may be used interchangeably with the term non-peptidyl linker.

The non-peptidyl polymer used for cross-linking may be selected from the group consisting of a biodegradable polymer including polyethylene glycol, polypropylene glycol, an ethylene glycol-propylene glycol copolymer, polyoxyethylated polyol, polyvinyl alcohol, polysaccharide, dextran, polyvinyl ethyl ether, polylactic acid (PLA) or polylactic-glycolic acid (PLGA), a lipid polymer, chitin, hyaluronic acid and a combination thereof. Specifically, polyethylene glycol (PEG) may be used, although not being limited thereto. In addition, their derivatives that are already known in the art and derivatives that can be easily prepared by a method known in the art may be included in the scope of the present invention.

For preparation of the long-acting hGH conjugate of the present invention, references such as Korean Patent No. 0725315 are disclosed in the present invention as cited references. Those skilled in the art can produce the long-acting hGH conjugate of the present invention by consulting the references, although not being limited thereto.

In another aspect, the present invention provides a lyophilized formulation of a long-acting hGH conjugate, comprising a lyophilized mixture of an aqueous solution comprising a long-acting hGH conjugate in which the hGH as a physiologically active peptide is linked to an immunoglobulin Fc region and an albumin-free solution comprising an acetate buffer, polysorbate 80 and mannitol.

The hGH, the immunoglobulin Fc region, the long-acting hGH conjugate, the albumin-free solution, the lyophilizing and the lyophilized formulation are the same as descried above.

In another aspect, the present invention provides a liquid formulation of a long-acting hGHconjugate, comprising a pharmaceutically effective amount of a long-acting hGHconjugate in which the hGHas a physiologically active peptide is linked to an immunoglobulin Fc region and an albumin-free stabilizer comprising a citrate buffer, polysorbate 80 and mannitol, the stabilizer not comprising an isotonic agent.

The hGH, the immunoglobulin Fc region, the long-acting hGHconjugate, the albumin-free stabilizer and the liquid formulation are the same as descried above.

In another aspect, the present invention provides a method for preparing the lyophilized formulation, comprising lyophilizing a long-acting hGH conjugate and an albumin-free solution comprising a buffer, a non-ionic surfactant and a sugar alcohol.

The long-acting hGH conjugate, the buffer, the non-ionic surfactant, the sugar alcohol, the albumin-free solution, the lyophilization and the lyophilized formulation are the same as descried above.

In another aspect, the present invention provides a method for reconstituting the lyophilized formulation, comprising adding a solution for reconstitution to the lyophilized formulation.

The lyophilized formulation and the reconstitution are the same as descried above.

As used herein, the term "solution for reconstitution" refers to a solution which is added to a lyophilized substance in solid state to reconstitute the same. The solution for reconstitution may be water for injection, e.g. sterilized distilled water, but is not specially limited thereto.

Also, the solution for reconstitution may further comprise a preservative.

As used herein, the term "preservative" refers to a substance that substantially reduces bacterial or fungal contamination in a formulation. Especially, it is comprised in the formulation to facilitate the production of a formulation for multiple dosing. Examples of preservative include octadecyl dimethyl benzyl ammonium chloride, hexamethonium chloride, benzalkonium chloride (mixture of alkylbenzyldimethylammonium chloride which has a long alkyl chain), and benzethonium chloride. Other types of preservatives include: aromatic alcohols such as phenol, butyl alcohol and benzyl alcohol; alkyl paraben such as methylparaben or propylparaben; catechol; resorcinol; cyclohexanol; 3-pentanol; and m-cresol, but are not limited thereto. The preservative in the liquid formulation of the present invention is specifically benzyl alcohol, m-cresol or phenol, more specifically benzyl alcohol, although not being limited thereto. The concentration of the preservative is specifically in a range from 0.001 to 0.9% (w/v), more specifically in a range from 0.1 to 0.9% (w/v), although not being limited thereto.

The formulation of the present invention reconstituted as described above may contain the long-acting hGH conjugate with a concentration ranging from 10 to 100 mg/mL, although not being limited thereto.

In another aspect, the present invention provides a kit comprising the lyophilized formulation and a solution for reconstitution.

The lyophilized formulation is the same as described above.

The kit comprises the lyophilized formulation and a solution for reconstitution and may further comprise a composition, solution or apparatus comprised of at least one other ingredient suitable for the reconstitution.

Hereinafter, the present invention is described in more detail with reference to examples. However, these examples are for illustrative purposes only, and the invention is not intended to be limited by these examples.

Preparation Example

Preparation of Long-Acting Human Growth Hormone (hGH) Conjugate

ALD-PEG-ALD, which is a polyethylene glycol with a molecular weight of about 3.4 kDa having aldehyde groups at both ends, was conjugated with the human growth hormone (hGH, molecular weight: 22 kDa), and then linked to the N-terminal of a human IgG4-derived aglycosylated Fc region (about kDa). Through this, the final product hGH-PEG-Fc conjugate (hereinafter, referred to as "long-acting hGH conjugate") which is a representative long-acting hGH conjugate of the present invention was prepared and purified.

Test Example 1

Evaluation of Lyophilized Formulation of Long-Acting hGH Conjugate (1) Analysis of Stability of Lyophilized Formulation of Long-Acting hGH Conjugate Depending on Concentration and Buffer After preparing lyophilized formulations comprising the long-acting hGH conjugate at concentrations described in Table 1, stability was analyzed after reconstitution. The effect of buffer and pH on the stability of the long-acting hGH conjugate was also analyzed.

As described in Table 1, the long-acting hGH conjugate was lyophilized with the given concentration using a pre-lyophilized formulation comprising a buffer, sodium chloride (NaCl), mannitol and polysorbate 80, which was then reconstituted using distilled water. The lyophilizing consisted of primary drying and secondary drying steps. The temperature gradient of the lyophilizing was set as freezing followed by primary drying (4° C.) and secondary drying (20° C.), as shown in FIG. 1. The reconstitution was conducted by dissolving the lyophilized formulation with distilled water of the same volume as that of the formulation before the lyophilization. The reconstituted liquid formulation was stored at 40° C. for 4 weeks and the stability was analyzed by ion exchange chromatography (IE-HPLC). The result is shown in Table 2. In Table 2, IE-HPLC (%) indicates the purity of the long-acting hGH conjugate at the given time.

TABLE 1

| | Conc. | Buffer | Salt | Sugar alcohol | Surfactant |
|---|---|---|---|---|---|
| Example 1 (Ex. 1) | 19.5 mg/mL | 20 mM sodium citrate (pH 5.2) | 150 mM NaCl | 5% mannitol | 0.005% polysorbate 80 |
| Ex. 2 | 78.0 mg/mL | 20 mM sodium citrate (pH 5.2) | 150 mM NaCl | 5% mannitol | 0.005% polysorbate 80 |
| Ex. 3 | 78.0 mg/mL | 20 mM sodium acetate (pH 5.6) | 150 mM NaCl | 5% mannitol | 0.005% polysorbate 80 |

TABLE 2

| | IE-HPLC (%) | | | |
|---|---|---|---|---|
| | Week 0 | Week 1 | Week 2 | Week 4 |
| Example 1 | 96.2 | 93.6 | 87.1 | 76.8 |
| Example 2 | 96.4 | 95.9 | 92.8 | 82.0 |
| Example 3 | 96.4 | 93.6 | 88.8 | 82.2 |

As seen from Table 2, the liquid formulation of a long-acting hGH conjugate showed no difference in stability depending on concentration after being stored at 40° C. for 4 weeks. Accordingly, it was confirmed that stability can be provided even to the long-acting hGH at high concentration.

Also, it was confirmed that the stability is maintained when the buffer and the pH were changed (compare Examples 2 and 3).

(2) Analysis of Stability and Solubility of Lyophilized Formulation of Long-Acting Human Growth Hormone (hGH) Conjugate Depending on Preservative Using the formulations of Example 2 (20 mM sodium citrate, pH 5.2, 150 mM sodium chloride, 5% mannitol, 0.005% polysorbate 80) and Example 3 (20 mM sodium acetate, pH 5.6, 150 mM sodium chloride, 5% mannitol, 0.005% polysorbate 80) of Test Example 1-(1) and an isotonic formulation prepared from the formulation of Example 3 (20 mM sodium acetate, pH 5.6, 4% mannitol, 0.005% polysorbate 80), the long-acting hGH conjugate was mixed at concentrations of 68.25 mg/mL and 58.5 mg/mL as described in Table 3, which were then lyophilized. After reconstituting using the solution for reconstitutions comprising preservatives described in Table 3, dissolution time and stability were measured. The product state was compared with unaided eyes. The lyophilizing and reconstitution were conducted in the same manner as described in Test Example 1-(1). The reconstituted liquid formulation was stored at 25° C. for 4 weeks and then stability was evaluated by ion exchange chromatography (IE-HPLC) and visual inspection. The result is shown in Table 4. In Table 4, IE-HPLC (%) indicates the purity of the long-acting hGH conjugate at the given time.

TABLE 3

| | Conc. | Buffer | Salt | Sugar alcohol | Surfactant | Preservative |
|---|---|---|---|---|---|---|
| Ex. 4 | 68.25 mg/mL | 20 mM sodium citrate (pH 5.2) | 150 mM NaCl | 5% mannitol | 0.005% polysorbate 80 | 0.3% m-cresol |
| Ex. 5 | 68.25 mg/mL | 20 mM sodium citrate (pH 5.2) | 150 mM NaCl | 5% mannitol | 0.005% polysorbate 80 | 0.9% benzyl alcohol |
| Ex. 6 | 68.25 mg/mL | 20 mM sodium acetate (pH 5.6) | 150 mM NaCl | 5% mannitol | 0.005% polysorbate 80 | 0.3% m-cresol |
| Ex. 7 | 68.25 mg/mL | 20 mM sodium acetate (pH 5.6) | 150 mM NaCl | 5% mannitol | 0.005% polysorbate 80 | 0.9% benzyl alcohol |
| Ex. 8 | 58.5 mg/mL | 20 mM sodium acetate (pH 5.6) | — | 4% mannitol | 0.005% polysorbate 80 | 0.3% m-cresol |
| Ex. 9 | 58.5 mg/mL | 20 mM sodium acetate (pH 5.6) | — | 4% mannitol | 0.005% polysorbate 80 | 0.3% phenol |

TABLE 4

| | IE-HPLC (%) | | | | Remarks |
|---|---|---|---|---|---|
| | Week 0 | Week 1 | Week 2 | Week 4 | |
| Example 4 | 96.7 | 93.2 | 90.0 | 83.7 | Precipitation occurred on week 3 |
| Example 5 | 96.7 | 92.6 | 89.8 | 83.1 | Precipitation occurred on week 3 |
| Example 6 | 96.6 | 93.1 | 89.4 | 87.7 | — |
| Example 7 | 96.5 | 93.1 | 89.6 | 87.5 | — |
| Example 8 | 97.6 | 95.4 | 92.3 | 88.1 | — |
| Example 9 | 97.4 | 95.3 | 92.4 | 87.4 | — |

As seen from Table 4, the stability of the long-acting hGH conjugate was maintained better in Examples 6 and 7 than in Examples 4 and 5. However, as can be seen from the results for Examples 6-9, there was no difference in the stability of the long-acting hGH conjugate depending on the kind of the preservatives. But, when the solution for reconstitution containing m-cresol was used, the resulting liquid formulation was hazy during the dissolution.

(3) Analysis of Solubility of Lyophilized Formulation of Long-Acting hGH Conjugate Depending on Conjugate Concentration Lyophilized formulations comprising the long-acting hGH conjugate at different concentrations were prepared and their product state and solubility upon reconstitution were evaluated. Using the formulation of Example 1 (20 mM sodium citrate, pH 5.2, 150 mM sodium chloride, 5% mannitol, 0.005% polysorbate 80) of Test Example 1-(1), the long-acting hGH conjugate was mixed at different concentrations as described in Table 5, which were then lyophilized. After reconstituting using distilled water, dissolution time was measured. The lyophilization and reconstitution were conducted in the same manner as described in Test Example 1-(1). The product state was compared with unaided eyes. The reconstitution was performed using an auto shaker set to 60° and 30 rpm. The time required for complete dissolution is given in Table 6.

TABLE 5

|  | Conc. | Buffer | Salt | Sugar alcohol | Surfactant |
| --- | --- | --- | --- | --- | --- |
| Ex. 1 | 19.5 mg/mL | 20 mM sodium citrate (pH 5.2) | 150 mM NaCl | 5% mannitol | 0.005% polysorbate 80 |
| Ex. 10 | 39.0 mg/mL | 20 mM sodium citrate (pH 5.2) | 150 mM NaCl | 5% mannitol | 0.005% polysorbate 80 |
| Ex. 11 | 58.5 mg/mL | 20 mM sodium citrate (pH 5.2) | 150 mM NaCl | 5% mannitol | 0.005% polysorbate 80 |
| Ex. 12 | 70.0 mg/mL | 20 mM sodium citrate (pH 5.2) | 150 mM NaCl | 5% mannitol | 0.005% polysorbate 80 |

TABLE 6

|  | Example 1 | Example 10 | Example 11 | Example 12 |
| --- | --- | --- | --- | --- |
| Dissolution time (sec) | 10 | 30 | 90 | 150 |

Although the product state of the lyophilized substance was stable regardless of concentration, more rigid cakes could be observed at higher concentrations. As seen from Table 6, the dissolution time was increased with concentration.

(4) Analysis of Stability and Solubility of Lyophilized Formulation of Long-Acting Human Growth Hormone (hGH) Conjugate Depending on Stabilizer Lyophilized formulations of the long-acting hGH conjugate were prepared using different stabilizers and their dissolution time, dissolution state and long-acting hGH conjugate stability were evaluated. Preformulations were prepared with the compositions described in Table 7, which were then used to freeze-dry the long-acting hGH conjugate at 78.0 mg/mL. After reconstituting using distilled water, dissolution time was measured. The lyophilization and reconstitution were conducted in the same manner as described in Test Example 1-(1). The product state was compared with unaided eyes. The reconstitution was performed using an auto shaker set to 60° and 30 rpm. The time required for complete dissolution is given in Table 8.

Also, after storing the reconstituted liquid formulation at 40° C. for 4 weeks, stability was evaluated by ion exchange chromatography (IE-HPLC). In Table 9, IE-HPLC (%) indicates the residual rate of the long-acting hGH conjugate at the given time relative to the initial value.

TABLE 7

|  | Conc. | Buffer | Salt | Sugar alcohol and other stabilizer | Surfactant |
| --- | --- | --- | --- | --- | --- |
| Ex. 13 | 78.0 mg/mL | 20 mM sodium citrate (pH 5.2) | 150 mM NaCl | 5% mannitol | 0.005% polysorbate 80 |
| Ex. 14 | 78.0 mg/mL | 20 mM sodium citrate (pH 5.2) | 150 mM NaCl | 5% mannitol | 0.02% polysorbate 80 |
| Ex. 15 | 78.0 mg/mL | 20 mM sodium citrate (pH 5.2) | 150 mM NaCl | 10% mannitol | 0.005% polysorbate 80 |
| Ex. 16 | 78.0 mg/mL | 20 mM sodium citrate (pH 5.2) | 150 mM NaCl | 2.5% mannitol | 0.005% polysorbate 80 |
| Ex. 17 | 78.0 mg/mL | 20 mM sodium citrate (pH 5.2) |  | 10% mannitol | 0.005% polysorbate 80 |
| Ex. 18 | 78.0 mg/mL | 20 mM sodium citrate (pH 5.2) |  | 5% mannitol 2% glycine | 0.005% polysorbate 80 |
| Ex. 19 | 78.0 mg/mL | 20 mM sodium citrate (pH 5.2) |  | 5% mannitol 5 mM histidine | 0.005% polysorbate 80 |

TABLE 8

|  | Ex. 13 | Ex. 14 | Ex. 15 | Ex. 16 | Ex. 17 | Ex. 18 | Ex. 19 |
| --- | --- | --- | --- | --- | --- | --- | --- |
| Dissolution time (sec) | 120 | 120 | 80 | 180 | 90 | 130 | 90 |

TABLE 9

|  | IE-HPLC (%) | | |
| --- | --- | --- | --- |
|  | Week 0 | Week 2 | Week 4 |
| Example 13 | 100.0 | 97.8 | 87.9 |
| Example 14 | 100.0 | 97.8 | 88.3 |
| Example 15 | 100.0 | 96.3 | 85.8 |
| Example 16 | 100.0 | 98.1 | 86.8 |
| Example 17 | 100.0 | 94.7 | 82.6 |
| Example 18 | 100.0 | 96.3 | 81.6 |
| Example 19 | 100.0 | 95.4 | 83.7 |

As seen from Table 8, high dissolution rate was obtained when the concentration of mannitol was high. Also, it was confirmed that the addition of 5 mM histidine leads to improved dissolution rate. The formulations of Examples 15 and 17 showed severe foaming during reconstitution as compared to the formulation of Example 19. As seen from Table 9, the stability after the dissolution was similar for each formulation. But, when sodium chloride was included as the stabilizer, the stability of the long-acting hGH conjugate was a little higher.

(5) Analysis of Solubility of Lyophilized Formulation Depending on Density of Lyophilized Substance and Concentration of Long-Acting hGH Conjugate Using the formulation of Example 19 (20 mM sodium citrate, pH 5.2, 5% (w/v) mannitol, 5 mM histidine, 0.005%

(w/v) polysorbate 80) of Test Example 1-(4), the solubility of the lyophilized substance depending on the long-acting hGH conjugate concentration was analyzed. Preformulations were prepared with the compositions described in Table 10 and then lyophilized. During the lyophilization, the preformulation was diluted 1-fold, ½-fold and ¼-fold using distilled water. The lyophilization consisted of primary drying and secondary drying steps. The temperature gradient of the lyophilization is shown in FIG. 1. The reconstitution was conducted by dissolving the lyophilized formulation with distilled water of the same volume as that of the formulation before the lyophilization. The reconstitution was performed using an auto shaker set to 60° and 30 rpm. The time required for complete dissolution is given in Table 11.

TABLE 10

| | Conc. | Buffer | Salt | Sugar alcohol and other stabilizer | Surfactant |
|---|---|---|---|---|---|
| Ex. 20 | 39.0 mg/mL | 20 mM sodium citrate (pH 5.2) | — | 5% mannitol 5 mM histidine | 0.005% polysorbate 80 |
| Ex. 21 | 48.8 mg/mL | 20 mM sodium citrate (pH 5.2) | — | 5% mannitol 5 mM histidine | 0.005% polysorbate 80 |
| Ex. 22 | 58.5 mg/mL | 20 mM sodium citrate (pH 5.2) | — | 5% mannitol 5 mM histidine | 0.005% polysorbate 80 |

TABLE 11

| | Example 20 | | | Example 21 | | | Example 22 | | |
|---|---|---|---|---|---|---|---|---|---|
| Dilution factor | 1 | ½ | ¼ | 1 | ½ | ¼ | 1 | ½ | ¼ |
| Dissolution time (sec) | 10 | 10 | 5 | 15 | 10 | 5 | 15 | 10 | 10 |

As seen from Table 11, it was confirmed that the dissolution rate is improved when the density of the lyophilized substance is decreased through dilution. Also, the dissolution rate increased similarly when the concentration of the long-acting hGH conjugate in the formulation (20 mM sodium citrate, 5% mannitol, 5 mM histidine, 0.005% polysorbate 80) was increased from 39.0 mg/mL to 48.8 mg/mL and to 58.5 mg/mL.

(6) Setting of Temperature Gradient for Lyophilization Process

The temperature gradient in Test Example 1-(1) (FIG. 1) was changed by increasing the primary drying time from 10 hours to 20 hours and subdividing the temperature of the primary drying step (4° C.) into two stages of −20° C. and −5° C. (FIG. 2). In the former temperature gradient, disruption of the lyophilized substance occurred because 3-5% of water remained in the lyophilized substance. When the temperature gradient was changed to that shown in FIG. 2, complete lyophilization could be achieved even with a larger volume (~5 mL).

(7) Analysis of Solubility of Lyophilized Formulation of Long-Acting hGH Conjugate Considering Osmotic Pressure Using the formulation (20 mM sodium acetate, pH 5.6, 5% (w/v) mannitol, 150 mM sodium chloride, 0.005% (w/v) polysorbate 80) of Test Example 1-(1) and (2), the concentration of the stabilizer was set considering osmotic pressure and the solubility of the lyophilized substance was analyzed. Preformulations were prepared as described in Table 12 and then lyophilized.

During the lyophilization, the preformulation was diluted ½-fold using distilled water. The lyophilization consisted of primary drying and secondary drying steps. The temperature gradient of the lyophilization was set as shown in FIG. 2. The reconstitution was conducted using distilled water containing 0.9% benzyl alcohol, which has the same volume as that of the formulation before the dilution.

The reconstitution was performed using an auto shaker set to 60° and 30 rpm. The time required for complete dissolution and the osmotic pressure measured after the reconstitution are shown in Table 13.

TABLE 12

| | Conc. | Buffer | Salt | Sugar alcohol and other stabilizer | Surfactant |
|---|---|---|---|---|---|
| Ex. 23 | 58.5 mg/mL | 20 mM sodium acetate (pH 5.6) | 150 mM NaCl | 5% mannitol | 0.005% polysorbate 80 |
| Ex. 24 | 58.5 mg/mL | 20 mM sodium acetate (pH 5.6) | 150 mM NaCl | — | 0.005% polysorbate 80 |
| Ex. 25 | 58.5 mg/mL | 20 mM sodium acetate (pH 5.6) | — | 5% mannitol | 0.005% polysorbate 80 |
| Ex. 26 | 58.5 mg/mL | 20 mM sodium acetate (pH 5.6) | 75 mM NaCl | 2.5% mannitol | 0.005% polysorbate 80 |

TABLE 13

| | Example 23 | Example 24 | Example 25 | Example 26 |
|---|---|---|---|---|
| Dissolution time (sec) | 30 | 180 | 15 | 60 |
| Osmotic pressure (mOsm/Kg) | 662 | 338 | 365 | 355 |

As seen from Table 13, the dissolution time was increased greatly when mannitol was removed. The osmotic pressure was higher than the isotonic range of 280-320 mOsm/Kg when the concentration of mannitol was 5% (w/v).

(8) Analysis of Solubility and Osmotic Pressure of Lyophilized Formulation of Long-Acting hGH Conjugate Depending on Mannitol Concentration Using the formulation (20 mM sodium acetate, pH 5.6, 5% (w/v) mannitol, 0.005% (w/v) polysorbate 80) of Test Example 1-(7), the solubility and osmotic pressure of the lyophilized substance depending on mannitol concentration were analyzed.

Preformulations were prepared as described in Table 14 and then lyophilized. The methods and conditions of the lyophilization and reconstitution were the same as described in Test Example 1-(7). The time required for complete dissolution and the osmotic pressure measured after the reconstitution are shown in Table 15.

TABLE 14

| | Conc. | Buffer | Salt | Sugar alcohol and other stabilizer | Surfactant |
|---|---|---|---|---|---|
| Ex. 23 | 58.5 mg/mL | 20 mM sodium acetate (pH 5.6) | 150 mM NaCl | 5% mannitol | 0.005% polysorbate 80 |
| Ex. 25 | 58.5 mg/mL | 20 mM sodium acetate (pH 5.6) | — | 5% mannitol | 0.005% polysorbate 80 |

TABLE 14-continued

|  | Conc. | Buffer | Salt | Sugar alcohol and other stabilizer | Surfactant |
|---|---|---|---|---|---|
| Ex. 27 | 58.5 mg/mL | 20 mM sodium acetate (pH 5.6) | — | 4.5% mannitol | 0.005% polysorbate 80 |
| Ex. 28 | 58.5 mg/mL | 20 mM sodium acetate (pH 5.6) | — | 4% mannitol | 0.005% polysorbate 80 |
| Ex. 29 | 58.5 mg/mL | 20 mM sodium acetate (pH 5.6) | — | 3.5% mannitol | 0.005% polysorbate 80 |

TABLE 15

|  | Ex. 23 | Ex. 25 | Ex. 27 | Ex. 28 | Ex. 29 |
|---|---|---|---|---|---|
| Dissolution time (sec) | 30 | 20 | 22 | 25 | 27 |
| osmotic pressure (mOsm/Kg) | 632 | 350 | 318 | 291 | 258 |

As seen from Table 15, isotonic osmotic pressure was observed when the concentration of mannitol was in the range from 4 to 4.5%. Although the dissolution time was longer as the mannitol concentration was lower, the change was smaller as compared to when sodium chloride was included.

(9) Analysis of Storage Stability of Lyophilized Formulation of Long-Acting hGH Conjugate at 4° C. and 25° C.

Using the formulation (20 mM sodium acetate, pH 5.6, 4% (w/v) mannitol, 0.005% (w/v) polysorbate 80) of Test Example 1-(8), the storage stability of the lyophilized substance was analyzed at 4° C. and 25° C. After storing the lyophilized formulation at 4° C. and 25° C. for 6 months, the stability was evaluated by ion exchange chromatography (IE-HPLC) after reconstitution. The initial solution for reconstitution was stored at 25° C. for 4 weeks in liquid state and then was evaluated by ion exchange chromatography (IE-HPLC) after reconstitution. In Table 16, IE-HPLC (%) indicates the purity of the long-acting hGH conjugate in the lyophilized substance at the given time. In Table 17, IE-HPLC (%) indicates the purity of the long-acting hGH conjugate in the reconstituted liquid formulation.

TABLE 16

|  | IE-HPLC (%) | | |
|---|---|---|---|
|  | Month 0 | Month 3 | Month 6 |
| 4° C. | 96.6 | 96.5 | 96.2 |
| 25° C. | 96.5 | 95.6 | 96.0 |

TABLE 17

| IE-HPLC (%) | | | |
|---|---|---|---|
| Week 0 | Week 1 | Week 2 | Week 4 |
| 96.6 | 93.1 | 89.4 | 87.7 |

As seen from Table 16, the stability of the lyophilized substance was maintained even after storing at 4° C. and 25° C. for 6 months. Also, the stability of the reconstituted formulation was maintained even after storing at 25° C. for 2 weeks.

Test Example 2

Evaluation of Liquid Formulation of Long-Acting hGH Conjugate (1) Analysis of Stability of Liquid Formulation of Long-Acting hGH Conjugate Depending on pH, Buffer, Isotonic Agent and Sugar Alcohol Concentration The effect of a buffer, an isotonic agent and the sugar alcohol concentration on the stability of the long-acting hGH conjugate was tested. Formulations prepared as described in Table 18 were stored at 25° C. for 0-4 weeks and then analyzed by ion exchange chromatography and size exclusion chromatography. In Tables 19 and 20, IE-HPLC (%) and SE-HPLC (%) indicate the residual rate of the long-acting hGH conjugate relative to the initial value, respectively (area %/start area %).

TABLE 18

|  | Long-acting hGH conjugate | pH | Buffer | Isotonic agent | Sugar alcohol and other stabilizer | Surfactant |
|---|---|---|---|---|---|---|
| Ex. 30 | 58.5 mg/mL | 5.2 | 20 mM sodium acetate | 75 mM NaCl | 2% mannitol | 0.005% polysorbate 80 |
| Ex. 31 | 58.5 mg/mL | 5.2 | 20 mM sodium acetate | — | 4% mannitol | 0.005% polysorbate 80 |
| Ex. 32 | 58.5 mg/mL | 5.6 | 20 mM sodium acetate | 75 mM NaCl | 2% mannitol | 0.005% polysorbate 80 |
| Ex. 33 | 58.5 mg/mL | 5.6 | 20 mM sodium acetate | — | 4% mannitol | 0.005% polysorbate 80 |
| Ex. 34 | 58.5 mg/mL | 5.6 | 20 mM histidine | 75 mM NaCl | 2% mannitol | 0.005% polysorbate 80 |
| Ex. 35 | 58.5 mg/mL | 5.6 | 20 mM histidine | — | 4% mannitol | 0.005% polysorbate 80 |

TABLE 19

| | IE-HPLC (%) | | | | |
|---|---|---|---|---|---|
|  | Week 0 | Week 1 | Week 2 | Week 3 | Week 4 |
| Example 30 | 100.0 | 98.5 | 97.0 | 95.3 | 91.9 |
| Example 31 | 100.0 | 98.9 | 96.9 | 94.8 | 91.9 |
| Example 32 | 100.0 | 96.9 | 94.9 | 92.2 | 87.2 |
| Example 33 | 100.0 | 97.8 | 96.7 | 94.7 | 90.2 |
| Example 34 | 100.0 | 97.8 | 94.7 | 92.4 | 86.5 |
| Example 35 | 100.0 | 96.1 | 93.0 | 88.4 | 82.9 |

TABLE 20

| | SE-HPLC (%) | | | | |
|---|---|---|---|---|---|
|  | Week 0 | Week 1 | Week 2 | Week 3 | Week 4 |
| Example 30 | 100.0 | 99.6 | 99.4 | 99.3 | 99.1 |
| Example 31 | 100.0 | 100.2 | 100.0 | 99.9 | 99.8 |
| Example 32 | 100.0 | 99.6 | 99.6 | 99.5 | 99.4 |
| Example 33 | 100.0 | 99.6 | 99.6 | 99.4 | 99.3 |
| Example 34 | 100.0 | 100.1 | 100.1 | 99.9 | 99.7 |
| Example 35 | 100.0 | 99.9 | 99.8 | 99.7 | 99.3 |

The IE-HPLC result showed that the long-acting hGH conjugate shows good stability under the condition of 20 mM sodium acetate (pH 5.2). And, the SE-HPLC result showed that the long-acting hGH conjugate was the most stable under the condition of 20 mM sodium acetate (pH 5.2) and 4% (w/v) mannitol.

(2) Analysis of Stability of Liquid Formulation of a Long-Acting hGH Conjugate Depending on Buffer The effect of a buffer as a stabilizer on the stability of the long-acting hGH conjugate was tested. Using the formulation (pH 5.2, 4% mannitol, 0.005% polysorbate 80) of Test Example 2-(1), formulations were prepared as described in Table 21. After storing at 25° C. for 0-4 weeks, the stability was analyzed by IE-HPLC and SE-HPLC. In Tables 22 and 23, IE-HPLC (%) and SE-HPLC (%) indicate the residual rate of the long-acting hGH conjugate relative to the initial value, respectively (area %/start area %).

TABLE 21

| | Long-acting hGH conjugate | pH | Buffer | Isotonic agent | Sugar alcohol and other stabilizer | Surfactant |
|---|---|---|---|---|---|---|
| Ex. 36 | 10.0 mg/mL | 5.2 | 20 mM sodium citrate | — | 4% mannitol | 0.005% polysorbate 80 |
| Ex. 37 | 10.0 mg/mL | 5.2 | 20 mM sodium acetate | — | 4% mannitol | 0.005% polysorbate 80 |
| Ex. 38 | 10.0 mg/mL | 5.2 | 20 mM histidine | — | 4% mannitol | 0.005% polysorbate 80 |
| Ex. 39 | 58.5 mg/mL | 5.2 | 20 mM sodium citrate | — | 4% mannitol | 0.005% polysorbate 80 |
| Ex. 31 | 58.5 mg/mL | 5.2 | 20 mM sodium acetate | — | 4% mannitol | 0.005% polysorbate 80 |
| Ex. 40 | 58.5 mg/mL | 5.2 | 20 mM histidine | — | 4% mannitol | 0.005% polysorbate 80 |

TABLE 22

| | IE-HPLC (%) | | | | |
|---|---|---|---|---|---|
| | Week 0 | Week 1 | Week 2 | Week 3 | Week 4 |
| Example 36 | 100.0 | 97.4 | 96.1 | 94.9 | 93.1 |
| Example 37 | 100.0 | 98.3 | 96.5 | 92.7 | 88.5 |
| Example 38 | 100.0 | 97.9 | 96.4 | 93.9 | 91.7 |
| Example 39 | 100.0 | 98.4 | 96.7 | 94.8 | 92.7 |
| Example 31 | 100.0 | 97.9 | 96.3 | 94.6 | 92.8 |
| Example 40 | 100.0 | 98.2 | 96.3 | 94.2 | 92.2 |

TABLE 23

| | SE-HPLC (%) | | | | |
|---|---|---|---|---|---|
| | Week 0 | Week 1 | Week 2 | Week 3 | Week 4 |
| Example 36 | 100.0 | 98.9 | 98.7 | 98.7 | 98.4 |
| Example 37 | 100.0 | 98.6 | 98.6 | 98.8 | 98.1 |
| Example 38 | 100.0 | 98.7 | 98.8 | 98.8 | 98.6 |
| Example 39 | 100.0 | 99.4 | 99.2 | 99.2 | 98.9 |
| Example 31 | 100.0 | 99.8 | 99.1 | 99.2 | 98.8 |
| Example 40 | 100.0 | 100.0 | 99.2 | 99.4 | 99.1 |

The IE-HPLC result showed that 10.0 mg/mL long-acting hGH conjugate was the most stable under the condition of sodium citrate. And, the SE-HPLC result showed that 10.0 mg/mL long-acting hGH conjugate showed good stability in the order of histidine and sodium citrate.

The IE-HPLC result showed that 58.5 mg/mL long-acting hGH conjugate showed good stability in the order of sodium acetate and sodium citrate. And, the SE-HPLC result showed that 58.5 mg/mL long-acting hGH conjugate showed good stability in the order of histidine and sodium citrate.

When the concentration of the long-acting hGH conjugate was in the range from 10 mg/mL to 58.5 mg/mL, the best stability was observed under the condition of 20 mM sodium citrate (pH 5.2), 4% mannitol and 0.005% polysorbate 80.

It will be apparent to those skilled in the art that various modifications and changes may be made without departing from the scope and spirit of the invention. Therefore, it should be understood that the above embodiment is not limitative, but illustrative in all aspects. The scope of the invention is defined by the appended claims rather than by the description preceding them, and therefore all changes and modifications that fall within metes and bounds of the claims, or equivalents of such metes and bounds are therefore intended to be embraced by the claims.

The invention claimed is:

1. A liquid formulation of a long-acting human growth hormone (hGH) conjugate, wherein the liquid formulation comprises a pharmaceutically effective amount of a long-acting human growth hormone conjugate in which the physiologically active human growth hormone is linked to an immunoglobulin Fc region and an albumin-free stabilizer,
    wherein the liquid formulation comprises a buffer, a non-ionic surfactant, a sugar alcohol, and preservative,
    wherein the sugar alcohol is included with a concentration ranging from 2% (w/v) to 4.5% (w/v);
    wherein the preservative is benzyl alcohol, m-cresol, or phenol;
    wherein the formulation does not comprise sodium chloride;
    wherein the buffer is a citrate buffer, an acetate buffer, or a histidine buffer;
    wherein the non-ionic surfactant is polysorbate 80;
    wherein the sugar alcohol is mannitol or sorbitol; and
    wherein the concentration of the long-acting hGH conjugate ranges from 58.5 to 60 mg/mL.

2. The liquid formulation of a long-acting human growth hormone conjugate according to claim 1, wherein the pH of the buffer ranges from 5.0 to 6.0.

3. The liquid formulation of a long-acting human growth hormone conjugate according to claim 1, wherein the concentration of the non-ionic surfactant ranges from 0.001% (w/v) to 0.05% (w/v) of the total volume of the formulation.

4. The liquid formulation of a long-acting human growth hormone conjugate according to claim 1, wherein the conjugate is in such a form that the human growth hormone is linked to the immunoglobulin Fc via a non-peptidyl polymer as a linker or via genetic recombination.

5. The liquid formulation of a long-acting human growth hormone conjugate according to claim 4, wherein the non-peptidyl polymer is a biodegradable polymer.

6. The liquid formulation of a long-acting human growth hormone conjugate according to claim 5, wherein the biodegradable polymer is selected from the group consisting of polyethylene glycol, polypropylene glycol, a copolymer of ethylene glycol and propylene glycol, a polyoxyethylated polyol, polyvinyl alcohol, a polysaccharide, dextran, polyvinyl ethyl ether, polylactic acid (PLA) and polylactic-glycolic acid (PLGA), a lipid polymer, chitin, hyaluronic acid and a combination thereof.

* * * * *